(12) United States Patent
Kitazawa et al.

(10) Patent No.: US 10,309,772 B2
(45) Date of Patent: Jun. 4, 2019

(54) ULTRASONIC THICKNESS REDUCTION INSPECTION METHOD/APPARATUS

(71) Applicant: Hitachi-GE Nuclear Energy, Ltd., Hitachi-shi, Ibaraki (JP)

(72) Inventors: Sou Kitazawa, Tokyo (JP); Naoyuki Kono, Tokyo (JP); Shinobu Okido, Hitachi (JP)

(73) Assignee: Hitachi-GE Nuclear Energy, Ltd., Hitachi-shi (JP)

( * ) Notice: Subject to any disclaimer, the term of this patent is extended or adjusted under 35 U.S.C. 154(b) by 199 days.

(21) Appl. No.: 15/360,010

(22) Filed: Nov. 23, 2016

(65) Prior Publication Data

US 2017/0153108 A1 Jun. 1, 2017

(30) Foreign Application Priority Data

Nov. 27, 2015 (JP) ................. 2015-231203

(51) Int. Cl.
| | |
|---|---|
| *G01B 17/02* | (2006.01) |
| *G01N 29/44* | (2006.01) |
| *G01N 29/50* | (2006.01) |
| *G01N 29/04* | (2006.01) |
| *G01N 29/11* | (2006.01) |
| *G01N 29/34* | (2006.01) |

(52) U.S. Cl.
CPC ............ *G01B 17/02* (2013.01); *G01N 29/04* (2013.01); *G01N 29/11* (2013.01); *G01N 29/343* (2013.01); *G01N 29/348* (2013.01); *G01N 29/4436* (2013.01); *G01N 29/50* (2013.01); *G01N 2291/015* (2013.01); *G01N 2291/0258* (2013.01); *G01N 2291/02854* (2013.01); *G01N 2291/044* (2013.01); *G01N 2291/262* (2013.01); *G01N 2291/2634* (2013.01); *G01N 2291/2636* (2013.01)

(58) Field of Classification Search
CPC ........ G01B 17/02; G01N 29/04; G01N 29/11; G01N 29/343; G01N 29/348; G01N 29/4436; G01N 29/50
See application file for complete search history.

(56) References Cited

U.S. PATENT DOCUMENTS

| | | | |
|---|---|---|---|
| 2015/0068311 A1 | 3/2015 | Tanaka et al. | |
| 2016/0033453 A1* | 2/2016 | Cegla ................. | G01B 17/02 73/602 |

FOREIGN PATENT DOCUMENTS

| | | | | |
|---|---|---|---|---|
| EP | 0981047 B1 * | 3/2008 | ........... | G01N 29/043 |
| JP | 61-111462 A | 5/1986 | | |
| JP | 2015-55559 A | 3/2015 | | |

\* cited by examiner

*Primary Examiner* — David Z Huang
(74) *Attorney, Agent, or Firm* — Crowell & Moring LLP

(57) ABSTRACT

Chirp waves generated in a transmitting/receiving unit is supplied to ultrasonic sensors. Signals output from the ultrasonic sensors are supplied to the transmitting/receiving unit and summed in a signal processing/recording unit. The signal processing/recording unit performs mutual correlation processing between the summed signals and the chirp waves and calculates a peak generation time difference. Necessity of exchanging a pipe is determined by calculating and recording the thickness of a pipe from the calculated time difference and calculating a difference between thicknesses measured in the past and the present.

12 Claims, 9 Drawing Sheets

ULTRASONIC THICKNESS REDUCTION INSPECTION METHOD/APPARATUS

BACKGROUND OF THE INVENTION

1. Field of the Invention

The present invention relates to a thickness reduction inspection method/apparatus for detecting a thickness reduction phenomenon of such as a pipe by an ultrasonic flaw detection method which is one of nondestructive inspection techniques.

2. Description of the Related Art

In recent years, since we have experienced rupture of a large diameter pipe due to thickness reduction in a nuclear power plant, a thickness reduction inspection by an ultrasonic thickness measurement method is simultaneously performed to corresponding portions of pipes in thermal power plants and nuclear power plants.

Inspection target portions and measurement methods are strictly managed based on technical codes established by The Japan Society of Mechanical Engineers (JASME), "technical codes for pipe wall thickness reduction management in Power Generation Facility Codes of JASME. Regarding a pipe portion which may cause thickness reduction, a facility manager measures, according to standards, a wall thickness in an axial direction and a circumferential direction at intervals of several tens mm based on multiple reflection echoes on a pipe inner surface.

Pipe thickness reduction phenomena to be measured are flow accelerated corrosion (FAC) and droplet impact erosion. FAC is a thickness reduction phenomenon in which corrosion is accelerated by facilitating mass transfer by flow near a pipe wall surface under flow conditions of a water single phase flow or a two phase flow forming a liquid film on a pipe wall.

When FAC occurs, pipe thickness reduction is gradually expanded over a wide range, and in the case where appropriate management is not performed, the FAC causes pipe rupture. Therefore, the appropriate management is critically important in thickness reduction management.

On the other hand, droplet impact erosion is a phenomenon in which the thickness of a pipe material is reduced by an impact force generated when droplets collide at a high speed on a pipe wall surface in a high-speed two-phase flow line.

In a nuclear plant, many pipes to be inspected are disposed at a high place where a scaffolding is needed, and also a heat insulating material is wound up around the pipes. Therefore, in the case where the thickness reduction inspection is performed, the inspection is performed after setting the scaffolding and removing the heat insulating material. Further, after measuring, it is necessary to wind up the heat insulating material again and remove the scaffolding.

Such work needs a large amount of labor and time and has a significant impact on inspection operation costs.

Therefore, a new inspection method is desired to reduce inspection items. The reduction of pipe inspection items is an issue common in industrial fields using a pipe such as the oil field and the gas field.

In recent years, various apparatuses and methods are proposed to efficiently inspect a pipe wall thickness and a pipe damage by using ultrasonic waves.

For example, JP 2015-055559 A discloses a method in which at least three ultrasonic transceivers are discretely provided to a pipe, and a position and a size of a damage and a scale adhered in the pipe due to corrosion and erosion generated in the pipe are measured based on ultrasonic wave signals transmitted and received among these transceivers.

According to JP 2015-055559 A, pulse ultrasonic waves output from one ultrasonic transceiver reach to a damage by propagating on a pipe wall of the pipe, and a part of the ultrasonic waves is reflected at the damage. Further, the reflected waves return to the ultrasonic transceiver, and also the reflected waves are detected in ultrasonic transceivers disposed at the other places. Then, based on a propagation time of the reflected waves, a position of a damage can be calculated by a method such as triangulation.

In addition, as a method to detect pitting corrosion of a pipeline laid underground or at the bottom of the sea, JP 61-111462 A discloses a pitting corrosion detection method in which a plurality of sensors and pulsars is connected to a pair of measuring circuits, the pulsars are sequentially driven at certain time intervals, in synchronization with this, the sensors are sequentially connected to the measuring circuits in a time division manner, and consequently several points can be detected by a pair of measuring apparatuses.

The sensors and the pulsars are mounted in an apparatus moving in a pipe called an inspection pig. According to this method, several sensors and pulsars can be mounted to the inspection pig by reducing a number of measuring circuits, and pitting corrosion of a large-diameter pipeline can be detected at a small pitch.

SUMMARY OF THE INVENTION

The technique described in JP 2015-055559 A can detect a pit (a small dent and hole generated on a metal surface since corrosive action is integrated) caused by corrosion/erosion. However, moderate thickness reduction caused by FAC cannot be detected since ultrasonic waves are not reflected.

Further, relatively a small number of ultrasonic transceivers are discretely provided, and therefore a continuous distribution status of thickness reduction in a pipe is not known.

In addition, according to the technique described in JP 61-111462 A, an inspection pig needs to insert in a pipe. However, it is difficult to insert the inspection pig into a nuclear power plant piping. In consideration of a possibility of an unexpected situation that the inspection pig cannot be recovered, it is nearly impossible to apply this technique to a nuclear power plant from a viewpoint of risk management and an inspection standard.

An object of the present invention is to realize an ultrasonic thickness reduction inspection method/apparatus which can efficiently inspect the occurrence and the distribution status of moderate pipe thickness reduction without inserting an inspection pig into a pipe.

To achieve the above-described object, the present invention is configured as described next.

In an ultrasonic thickness reduction inspection method, a plurality of ultrasonic sensors is disposed on a surface of an inspection target, the plurality of ultrasonic sensors is excited by a pulse compression wave signal, ultrasonic waves are supplied in the inspection target, signals in which the plurality of ultrasonic sensors is excited by a plurality of echoes from the inside of the inspection target by the ultrasonic waves supplied in the inspection target are received, the plurality of received echo signals is summed, from cross correlation between signals summing the plurality of echo signals and the pulse compression wave signal, a time difference between a first peak of the summed signal and a first peak of the pulse compression wave signal, and a change in a thickness of the inspection target is detected based on the calculated time difference.

An ultrasonic thickness reduction inspection apparatus includes a plurality of ultrasonic sensors, a transmitting/receiving unit, and a signal processing/recording unit. The ultrasonic sensors are disposed on a surface of an inspection target. The transmitting/receiving unit excites the plurality of ultrasonic sensors by a pulse compression wave signal, supplies ultrasonic waves in the inspection target, and receives signals in which the plurality of ultrasonic sensors is excited by a plurality of echoes from the inside of the inspection target by the ultrasonic waves supplied in the inspection target. The signal processing/recording unit sums the plurality of echo signals received by the transmitting/receiving unit, calculates, from cross correlation between signals summing the plurality of echo signals and the pulse compression wave signal, a time difference between a first peak of the summed signal and a first peak of the pulse compression wave signal, and detect a change in a thickness of the inspection target based on the calculated time difference.

A pipe thickness reduction inspection method/apparatus can be realized which can efficiently inspect the occurrence and the distribution state of moderate thickness reduction of a pipe without inserting an inspection pig into the pipe.

DESCRIPTION OF THE PREFERRED EMBODIMENTS

Hereinafter, embodiments of the present invention will be described in detail with reference to drawings.

EMBODIMENTS

First Embodiment

Figure 1:
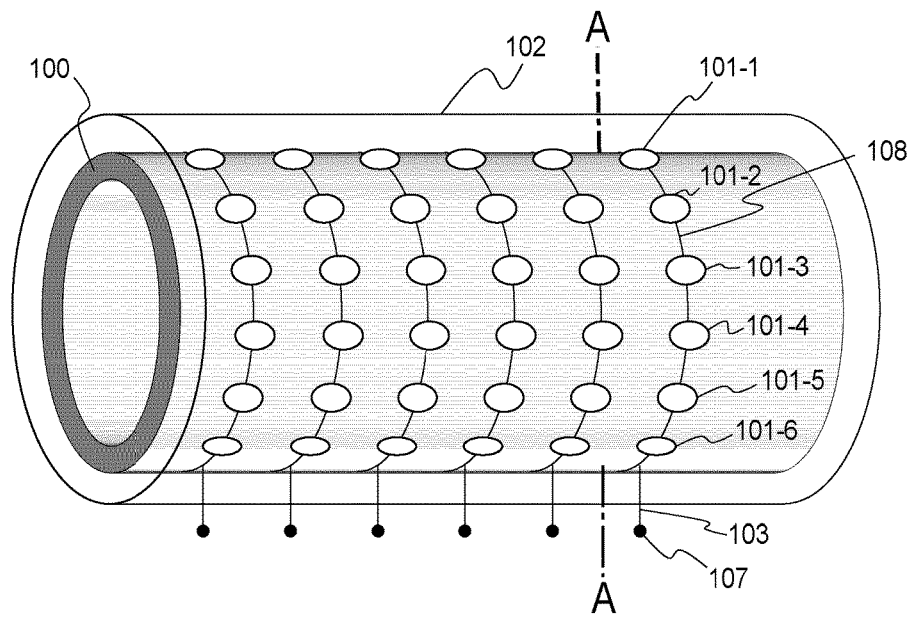
FIG. 1 is a view schematically indicating a state in which a sensor according to a first embodiment of the present invention is attached to a pipe.
Figure 2:
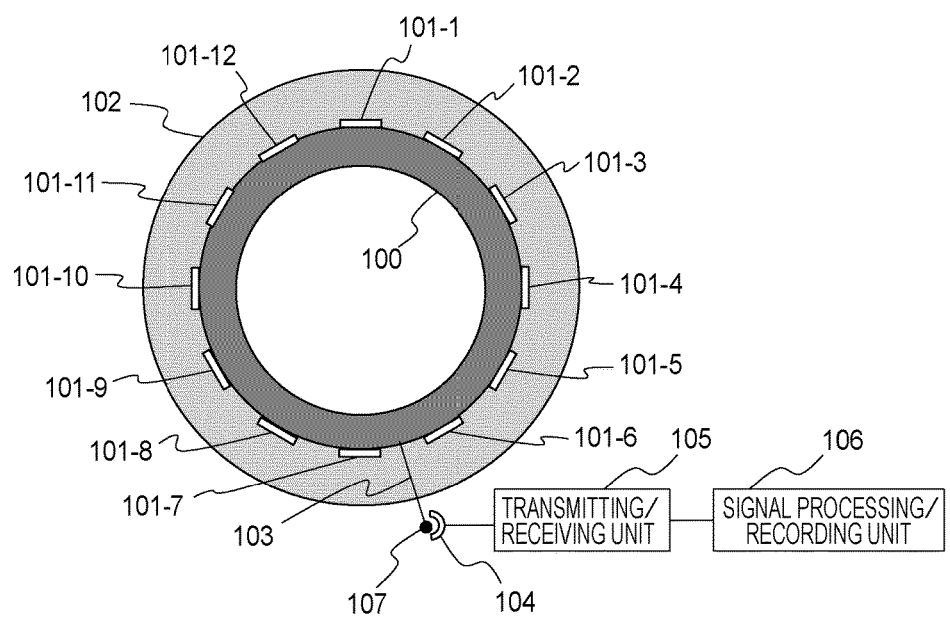
FIG. 2 is a sectional view along line A-A illustrated in FIG. 1.

FIG. 1 is a view schematically indicating a state in which a sensor according to a first embodiment of the present invention is attached to a pipe. FIG. 2 is a sectional view along line A-A illustrated in FIG. 1. In FIGS. 1 and 2, an insulating material 102 is attached around a pipe 100, and between the pipe 100 and the insulating material 102, a plurality of ultrasonic sensors 101-1 to 101-12 for thickness reduction inspection is attached at equal intervals in a circumferential direction of the pipe 100.

Ultrasonic vibrators are incorporated in the ultrasonic sensors 101-1 to 101-12. Ultrasonic vibrators are formed by, for example, piezoelectric ceramic of such as lead zirconate titanate (PZT), a single crystal, a composite piezoelectric body combined with the material and polymer, or a polymer piezoelectric body represented by such as polyvinylidene fluoride (PVDF). The ultrasonic vibrator converts a voltage into an ultrasonic wave and sends it in a pipe, or converts an echo reflected in the pipe into an electric signal.

To simplify a description, in FIGS. 1 and 2, twelve ultrasonic sensors are followed by reference signs. A number of the ultrasonic sensors is determined to an appropriate number from a measured pitch in a diameter direction and a circumferential direction of the pipe 100, and the measured pitch in the circumferential direction is typically approximately 5 to 10 cm. In addition, plural sets of ultrasonic sensors similar to the ultrasonic sensors 101-1 to 101-12 are arranged in an axial direction of the pipe 100.

The ultrasonic sensors 101-1 to 101-12 are connected in a circumferential direction by a wiring 108, and also a part of the wiring 108 is connected to a signal lead-out line 103 penetrating the insulating material 102. However, the signal lead-out line 103 does not necessarily penetrate the insulating material 102. For example, the signal lead-out line 103 may be led out to the outside from such as a space provided when the insulating material 102 is attached.

A connection terminal 107 is attached at a tip of the signal lead-out line 103. The connection terminal 107 connects to a connection terminal 104 of a transmitting/receiving unit 105 during measuring and can transmit and receive an ultrasonic waveform signal from the transmitting/receiving unit 105. Regarding the other ultrasonic sensors disposed in an axial direction of the pipe 100, similarly, the connection terminal 104 of the transmitting/receiving unit 105 and a connection terminal of each of them are connected during measuring.

The ultrasonic waveform signal received by the transmitting/receiving unit 105 is recorded in a memory (storage unit) after an appropriate signal processing is performed by a signal processing/recording unit 106. As described above, a plurality of ultrasonic sensors similar to the ultrasonic sensors 101-1 to 101-12 connected in a circumferential direction is disposed side by side in an axial direction of the pipe 100. An installation pitch of these ultrasonic sensors may be determined as requested. Typically, the installation pitch in the axial direction is approximately 5 to 10 cm.

When a wall thickness of the pipe 100 is measured, a pulsar signal issued from the transmitting/receiving unit 105 simultaneously drives (excites) the plurality of ultrasonic sensors 101-1 to 101-12 connected by the wiring 108. The plurality of ultrasonic sensors 101-1 to 101-12 is excited by an echo from the inside of the pipe 100, and a signal summing ultrasonic waveform signals measured at the installation position is sent to the transmitting/receiving unit

105. Then, the summed sign is recorded after signal processing is performed to the signal. Such the signal processing will be described in detail with reference to FIG. 3.

Figure 3:
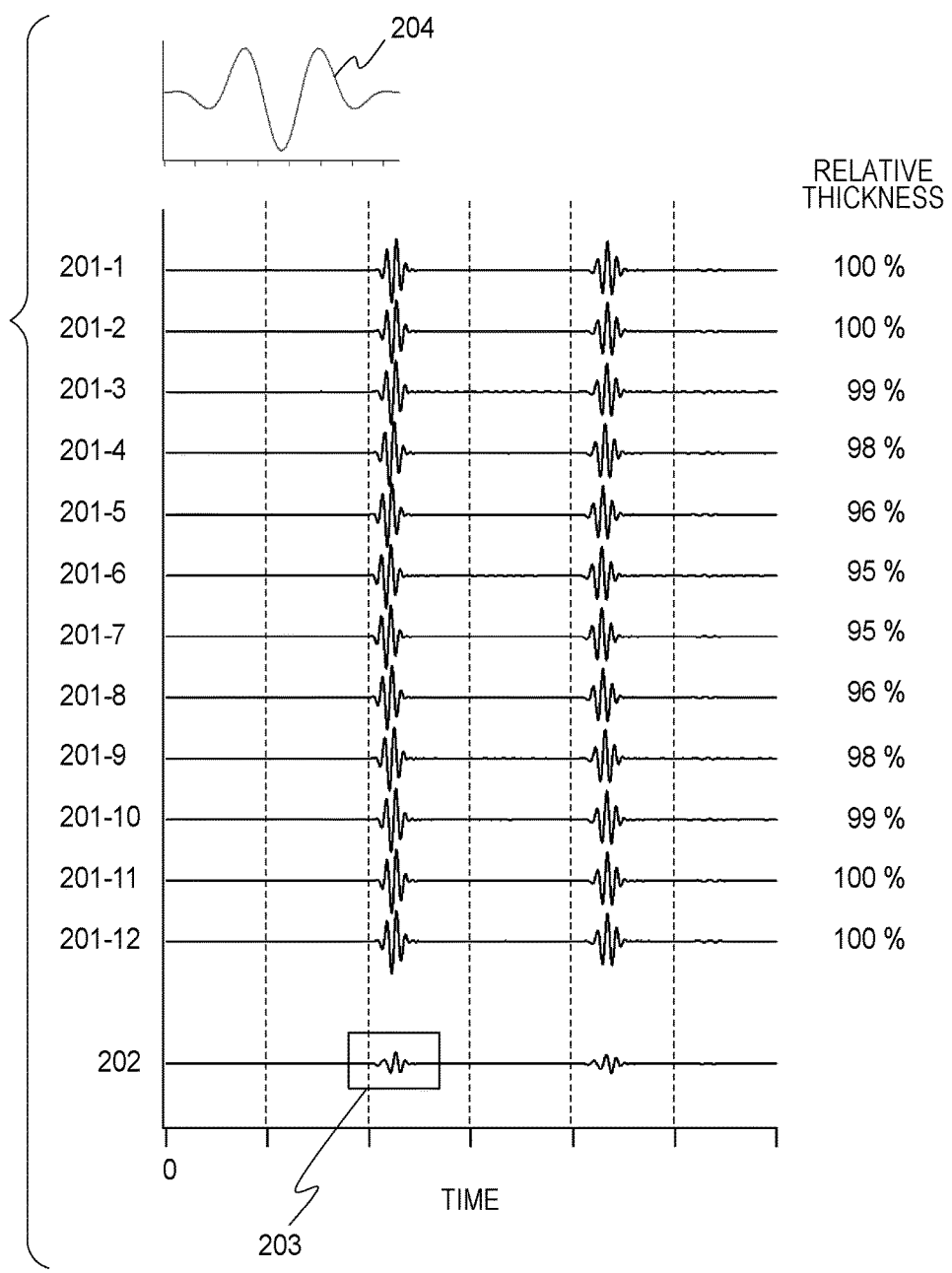
FIG. 3 is a diagram indicating a signal waveform received from an ultrasonic sensor in an example different from the present invention.

FIG. 3 is a view illustrating signal waveforms received from the ultrasonic sensors 101-1 to 101-12 in an example different from the present invention. Reference signs "201-1" to "201-12" in FIG. 3 are ultrasonic waveform signals output from the ultrasonic sensors 101-1 to 101-12 in the case where a pulse waveform 204 is used as an input waveform to the ultrasonic sensors 101-1 to 101-12. A horizontal axis of FIG. 3 indicates a time, and a time passes from the left to the right in FIG. 3.

A relative thickness of the pipe 100 at the positions where the ultrasonic sensors 101-1 to 101-12 are disposed is indicated at the right end in FIG. 3 (indicated by percentage). The thicknesses of the ultrasonic sensors 101-6 and 101-7 are thinnest and 95% of the thickness of a portion where the ultrasonic sensor 101-1 is disposed. In each of ultrasonic waveform signals 201-1 to 201-12, a first echo and a second echo are appeared in an inner surface of the pipe 100. As the thickness is decreased, a time when the echo appears is advanced.

A waveform in which ultrasonic waveform signals 201-1 to 201-12 are summed, specifically summed ultrasonic waveform signal 202, is observed in the transmitting/receiving unit 105. A shape of the summed ultrasonic waveform signal 202 is variously changed depending on phase differences among ultrasonic waveform signals 201-1 to 201-12. Positive and negative peaks of the ultrasonic waveform signals 201-1 to 201-12 are mutually cancelled, and the strength of the summed ultrasonic waveform signal 202 is significantly reduced. As a result, the summed ultrasonic waveform signal 202 may be buried in noise and not be detected.

Figure 4:
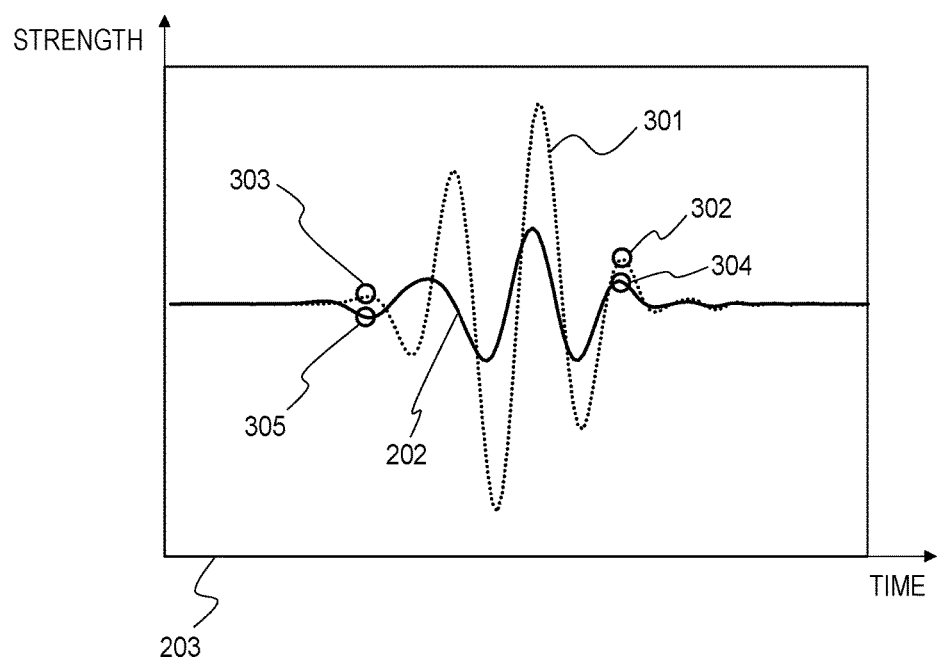
FIG. 4 is an enlarged diagram of a region near a first echo of a summed ultrasonic waveform signal in FIG. 3.

FIG. 4 is an enlarged diagram of a region 203 near a first echo of the summed ultrasonic waveform signal 202. In FIG. 4, a summed ultrasonic waveform signal 301 (a broken line) is indicated with the summed ultrasonic waveform signal 202 (a solid line). The summed ultrasonic waveform signal 301 is a summed ultrasonic waveform signal in the case where all of the relative thicknesses at the positions where ultrasonic sensors 101-1 to 101-12 are disposed are 100% (specifically, a state in which thickness reduction is not detected at all).

Due to the phase differences, a peak strength of the summed ultrasonic waveform signal 202 becomes lower than a peak strength of the summed ultrasonic waveform signal 301. The thickest portion corresponds to a peak 302 or 304, and the thinnest portion corresponds to a peak 303 or 305.

However, the peaks 303 and 305 are detected at almost the same time although positive and negative peaks are reversed. Therefore, it is difficult to accurately determine the occurrence of thickness reduction by comparing low strength sum signals.

To solve this issue, in the present invention, a pulse wave using a pulse compression method is set to an input wave from the ultrasonic sensor 101-1 to the ultrasonic sensor 101-12. A pulse compression method is a technique to compress a pulse wave by a signal processing when a signal is received and to simultaneously obtain a high SN ratio and a high time resolution. A waveform is compressed by performing cross correlation processing between a transmitted pulse waveform and a received waveform after the signal is received. As a representative coded pulse wave, a chirp wave is used in which a frequency is changed (increased or decreased) with time. In embodiments described herein, the chirp wave is used. However, in the present invention, without being limited to a chirp wave, a signal of which an autocorrelation function is a delta function type can be also used. For example, various waveforms including a barker type, a complementary sequence, and an M sequence can be used.

In a chirp wave pulse compression method, a frequency modulation signal in which a frequency is changed with time is used, and the method is widely used in such as the radar field. Specifically, while using a pulse waveform (chirp wave) in which a frequency is linearly changed with time is used as an input signal, a pulse width is compressed by signal processing when a signal is received, and a signal-to-noise ratio (SN ratio) and a high time resolution are simultaneously obtained. Compression of the pulse width can be realized by cross correlation processing of the input signal and the received signal.

Figure 5:
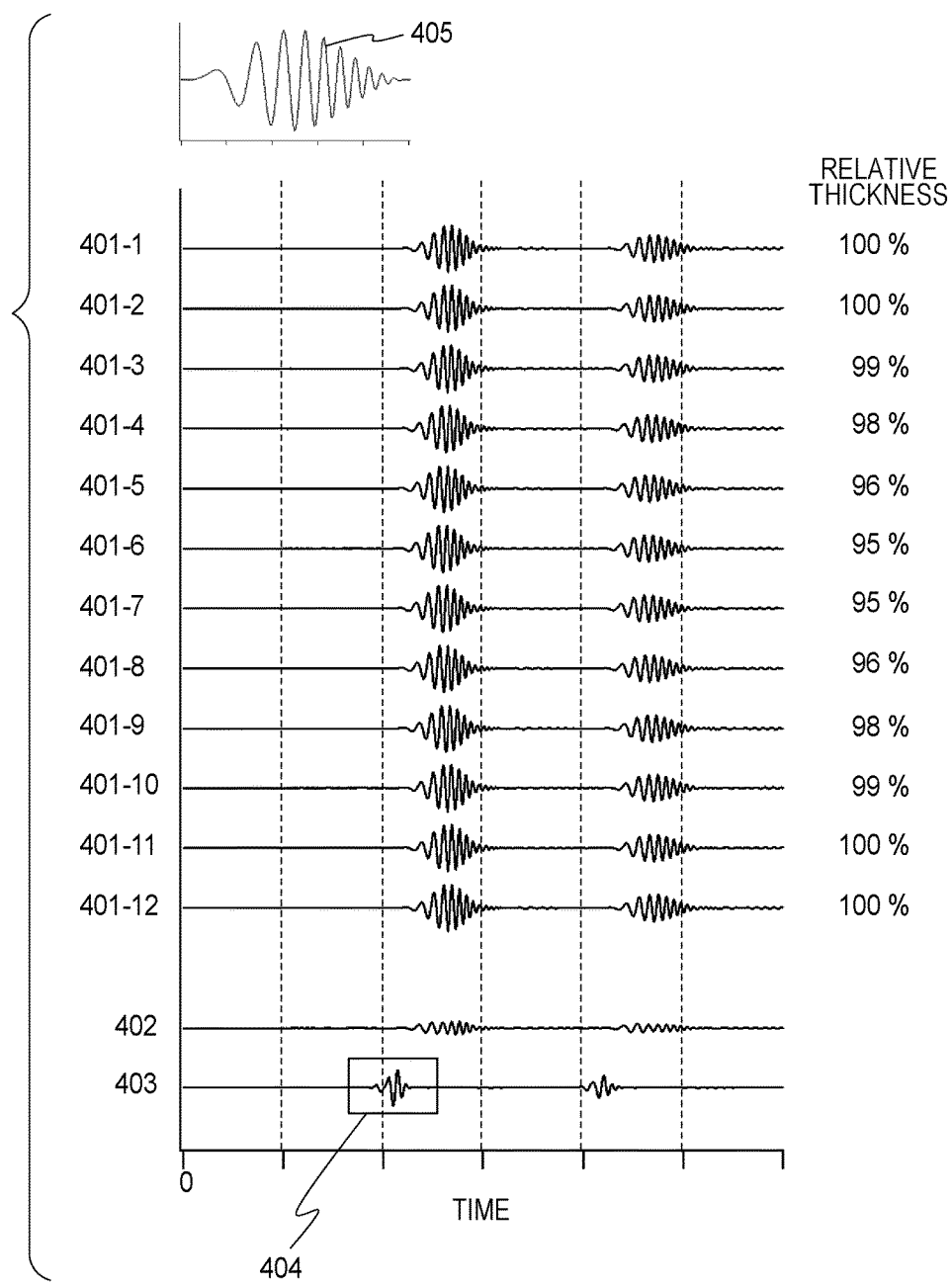
FIG. 5 is a waveform diagram according to the first embodiment of the present invention.

FIG. 5 is a waveform diagram according to the first embodiment of the present invention and indicates ultrasonic waveform signals 401-1 to 401-12 output from the ultrasonic sensors 101-1 to 101-12 in the case where a chirp wave 405 is used as an input waveform to the ultrasonic sensors 101-1 to 101-12. A horizontal axis of FIG. 5 indicates a time, and a time passes from the left to the right in FIG. 5.

In FIG. 5, as in the case where the pulse waveform 204 illustrated in FIG. 4 is used, a first echo in a thin portion appears at the earliest time. The ultrasonic waveform signal 402 is summed from the ultrasonic waveform signals 401-1 to 401-12. Due to phase differences, strength of the ultrasonic waveform 402 is lowered in comparison with each waveform before summation.

A waveform in which cross correlation processing between the ultrasonic waveform signal 402 and the chirp wave 405 is performed is a compressed ultrasonic waveform signal 403. A peak appears at a time when cross correlation between the ultrasonic waveform signal 402 and the chirp wave 405 becomes highest. Therefore, echo peak positions of the ultrasonic waveform signals 401-1 to 401-12 are different. A plate thickness (wall thickness) is calculated by multiplying a peak position time of the compressed ultrasonic waveform signal 403 by a sonic speed (for example, a longitudinal wave sonic speed of a steel material forming a pipe 5,900 m/s).

Figure 6:
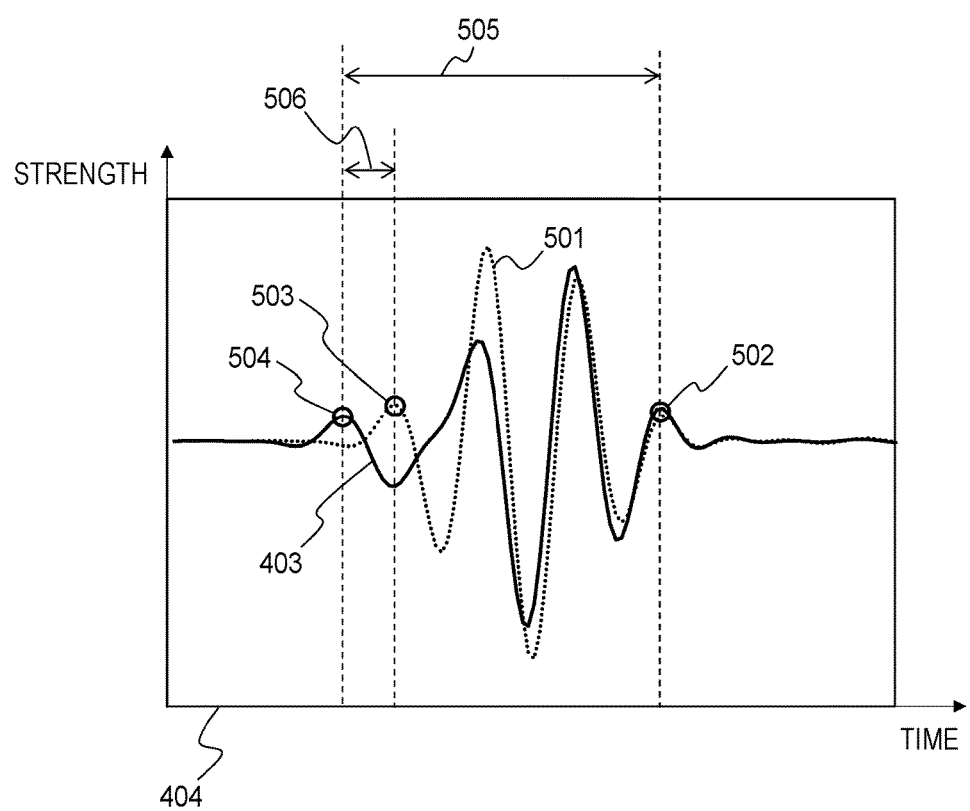
FIG. 6 is an enlarged diagram of a region near a first echo of a compressed ultrasonic waveform signal according to the first embodiment of the present invention.

FIG. 6 is an enlarged diagram of a region 404 near a first echo of the compressed ultrasonic waveform signal 403 (solid line) according to the first embodiment of the present invention. For comparison, FIG. 6 illustrates a compressed ultrasonic waveform signal 501 in the case where all of the relative thicknesses of the positions from the ultrasonic sensor 101-1 to the ultrasonic sensor 101-12 are 100% (in other words, a state in which a thickness reduction is not caused at all).

In FIG. 6, the compressed ultrasonic waveform signals 403 and 501 are different from a simple synthesized waveform, and a peak strength is not affected by a phase difference of ultrasonic waveform signals before summation.

Specifically, a peak of the ultrasonic waveform signals before summation is not mutually cancelled and not weakened. The compressed ultrasonic waveform signals 403 and 501 indicate a correlation degree with an input waveform, and a time expansion 505 thereof is reflected by a thickness distribution. For example, a right end peak 502 of the compressed ultrasonic waveform signal 403 is contributed by a signal component of the position where the thickness is 100%, and a left end peak 504 (first peak) is contributed by a signal component of the position where the thickness is 95%. A value obtained by multiplying a time difference 506 between the left end peaks 503 (the first peak) and 504 (the first peak) of the compressed ultrasonic waveform signal 501 in which thickness reduction is not detected by a sonic speed is equal to a thickness difference.

A thickness reduction phenomenon is a phenomenon changing with time. Therefore, as illustrated in FIG. 6, by periodically comparing with a summed signal before thickness reduction occurs (for example, the compressed ultrasonic waveform signal 501), it is possible to determine the occurrence of thickness reduction in a range from the ultrasonic sensors 101-1 to 101-12. Further, from a change in time expansion of the compressed ultrasonic waveform signal, the amount of a thickness change can be accurately estimated. A time expansion of the compressed ultrasonic waveform signal depending on thickness variation generated during manufacturing may be detected. However, a change with time from a reference state is detected for a thickness reduction phenomenon, and therefore there is no problem.

Figure 7:
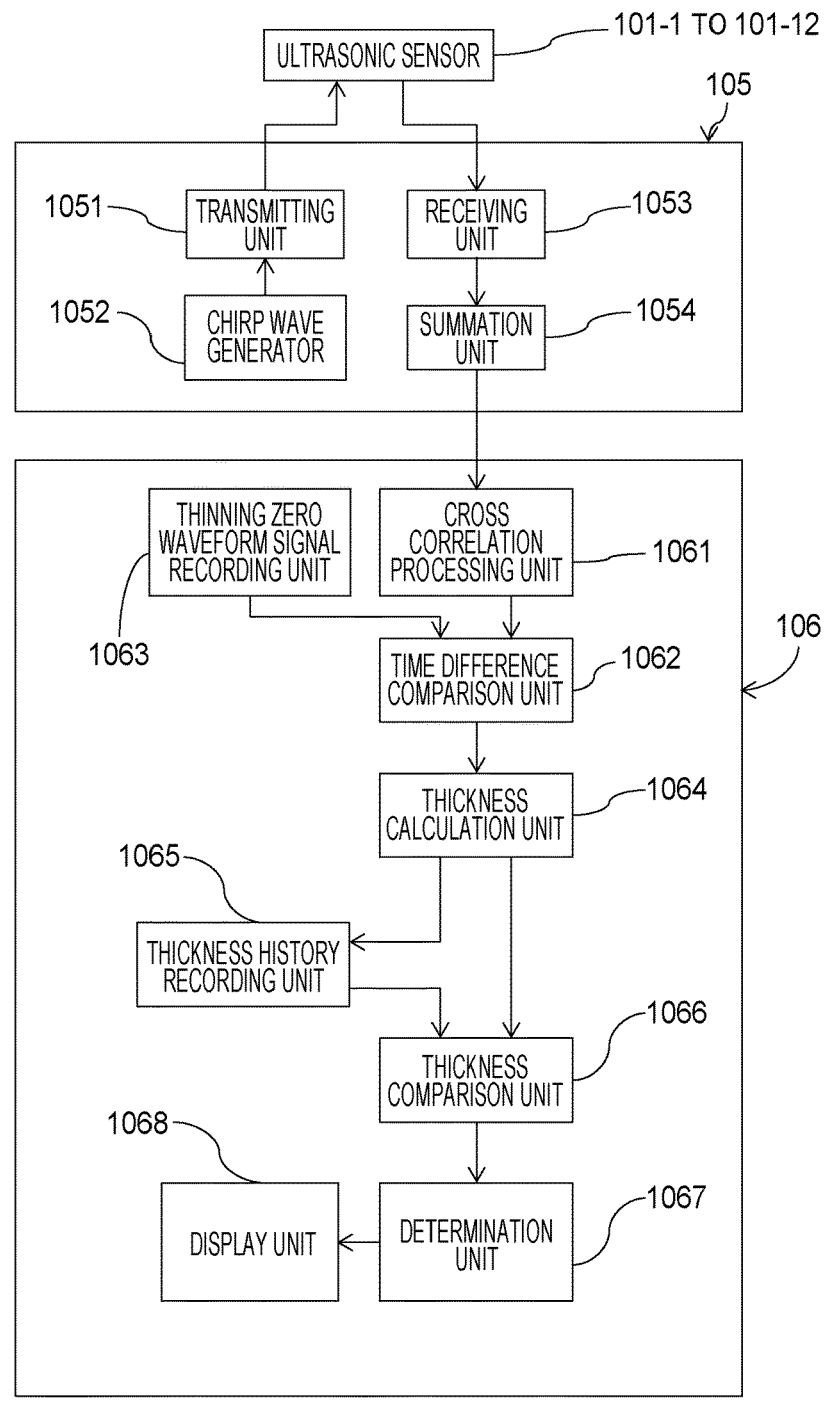
FIG. 7 is an internal block diagram of a transmitting/receiving unit and a signal processing/recording unit according to the first embodiment of the present invention.

FIG. 7 is an internal block diagram of the transmitting/receiving unit 105 and the signal processing/recording unit 106. In FIG. 7, the transmitting/receiving unit 105 includes a transmitting unit 1051, a chirp wave generator 1052, a receiving unit 1053, and a summation unit 1054. Chirp waves generated in the chirp wave generator 1052 are supplied to the ultrasonic sensors 101-1 to 101-12 as an input signal by the transmitting unit 1051, and ultrasonic waves are supplied in the pipe 100 by being excited by the chirp waves. The ultrasonic sensors 101-1 to 101-12 receive echo signals from the pipe 100 and output the received echo signals. Signals (echo signals) output from the ultrasonic sensors 101-1 to 101-12 are supplied to the receiving unit 1053 and summed in the summation unit 1054.

The signal processing/recording unit 106 includes a cross correlation processing unit 1061, a time difference comparison unit 1062, a thickness reduction zero waveform signal recording unit 1063, a calculation unit 1064, a thickness history recording unit 1065, a thickness comparison unit 1066, a determination unit 1067, and a display unit 1068.

A signal summed by the summation unit 1054 of the transmitting/receiving unit 105 is supplied to the cross correlation processing unit 1061, and cross correlation processing is performed between the summed signal and a chirp waveform.

Then, in the time difference comparison unit 1062, a generation time difference between the peak 503 of the signal 501 recorded in the thickness reduction zero waveform signal recording unit 1063 and the peak 504 of the summed signal 403 is calculated. Next, a time difference calculated by the time difference comparison unit 1062 is supplied to the thickness calculation unit 1064. The thickness of the pipe 100 is calculated. The calculated thickness value is recorded in the thickness history recording unit 1065 and supplied to the thickness comparison unit 1066. The thickness history recording unit 1065 records a history from a reference state (initial thickness) of the pipe 100. The thickness comparison unit 1066 calculates a difference between the thicknesses measured in the past and the present and a decrease ratio therebetween and supplies them to the determination unit 1067.

The determination unit 1067 determines necessity of exchanging the pipe 100 based on the thickness difference calculated by the thickness comparison unit 1066 and causes the display unit 1068 to display a determination result and a thickness reduction state. The determination unit 1067 may cause the display unit 1068 to display only a thickness reduction state of the pipe 100.

As described above, according to the first example of the present invention, a pipe thickness is calculated by supplying a chirp wave signal by a pulse compression method to an ultrasonic sensor, supplying ultrasonic waves to a pipe, and calculating a peak time difference by correlation between a summed waveform of an echo signal from the ultrasonic sensor and a signal in the case of no thickness reduction. Therefore, a pipe thickness reduction inspection method/apparatus capable of efficiently inspecting the occurrence and the distribution state of moderate pipe thickness reduction can be realized without inserting an inspection pig into a pipe.

Specifically, moderate thickness reduction generated by such as FAC can be efficiently detected from a pipe external surface.

Second Embodiment

Next, a second embodiment of the present invention will be described next.

Figure 8:
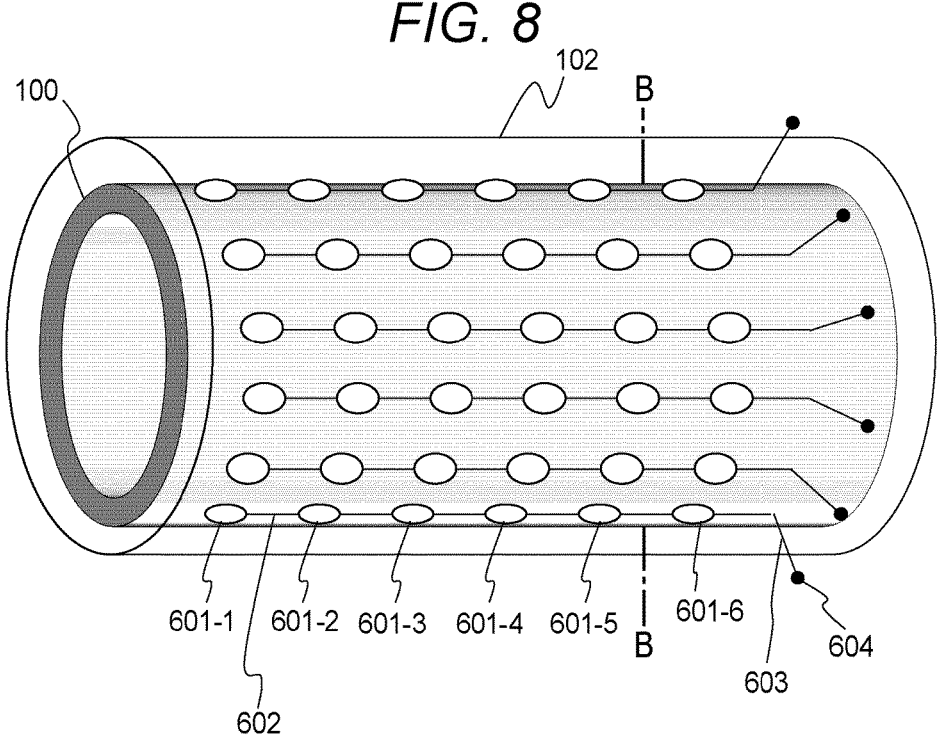
FIG. 8 is a view schematically indicating a state in which an ultrasonic sensor according to a second embodiment of the present invention is attached to a pipe.
Figure 9:
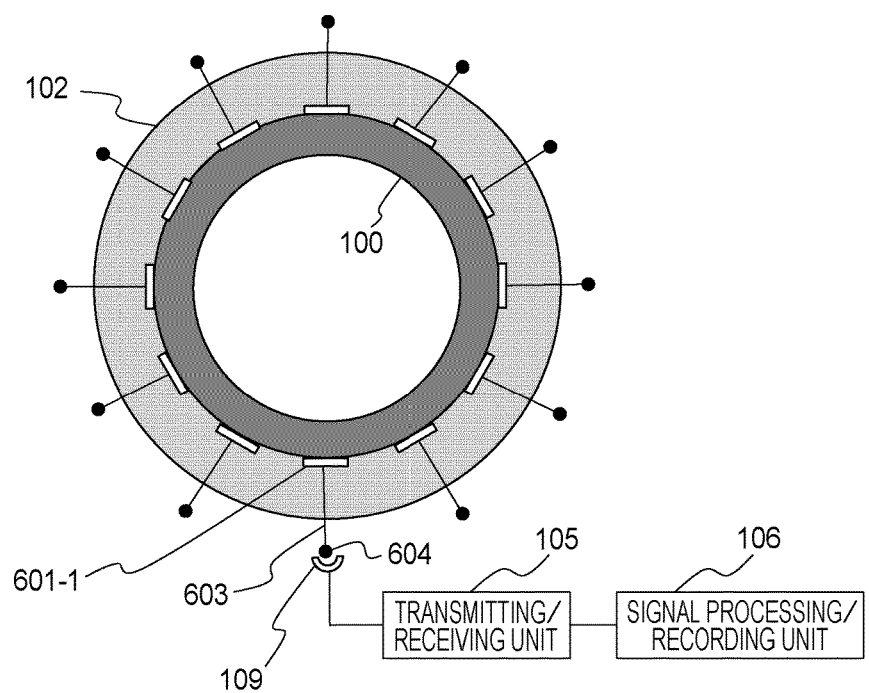
FIG. 9 is a sectional view along line B-B illustrated in FIG. 8.

FIG. 8 is a view schematically indicating a state in which an ultrasonic sensor according to the second embodiment of the present invention is attached to a pipe. FIG. 9 is a sectional view along line B-B illustrated in FIG. 8.

In FIGS. 8 and 9, an insulating material 102 is attached around a pipe 100, and a plurality of ultrasonic sensors 601-1 to 601-6 for thickness reduction inspection is disposed in a space between the pipe 100 and the insulating material 102. To simplify a description, FIG. 8 indicates a case where six ultrasonic sensors are provided. However, a number of the ultrasonic sensors is determined to an appropriate number from a measured pitch in an axial direction. The ultrasonic sensors 601-1 to 601-6 are connected in an axial direction by a wiring 602, and also a part of the wiring 602 is connected to a signal lead-out line 603 penetrating the insulating material 102. However, the signal lead-out line 603 does not necessarily penetrate the insulating material 102. For example, the signal lead-out line 603 may be led out to the outside from such as a space provided when the insulating material 102 is attached.

A connection terminal 604 is attached at a tip of the signal lead-out line 603. The connection terminal 604 can transmit and receive an ultrasonic waveform signal from a transmitting/receiving unit 105 by connecting to a connection terminal 109 of the transmitting/receiving unit 105 during measuring. The ultrasonic waveform signal received by the transmitting/receiving unit 105 is recorded in a memory after appropriate signal processing is performed in a signal processing/recording unit 106.

A plurality of ultrasonic sensors similar to the ultrasonic sensors 601-1 to 601-6 connected in an axial direction of the pipe 100 is disposed side by side in a circumferential direction of the pipe 100. An installation pitch in this case may be determined as requested. Typically, the installation pitch in an axial direction is approximately 5 to 10 cm.

When a thickness is measured, a pulsar signal issued from the transmitting/receiving unit 105 simultaneously drives the plurality of ultrasonic sensors 601-1 to 601-6 connected by the wiring 602, and a signal summing ultrasonic waveform signals measured at each installation position is sent to the transmitting/receiving unit 105 and recorded after appropriate signal processing is performed. The transmitting/receiving unit 105 and the signal processing/recording unit 106 have a configuration as in the first embodiment. The signal processing is also configured as in the first embodiment. Therefore descriptions thereof will be omitted.

Effects as in the first embodiment can be obtained in the second embodiment of the present invention.

A connecting method of ultrasonic sensors is not limited to the method described in the first or second embodiments and can be arbitrarily determined. For example, ultrasonic sensors may be connected in a circumferential direction and an axial direction, and a part of or all of ultrasonic sensors may be connected. In addition, for example, there is a method in which a region which may cause thickness reduction is analyzed in a fluid analysis and measured fluid phenomenon, and a sensor in the region is connected.

Third Embodiment

Next, a third embodiment of the present invention will be described next.

Figure 10:
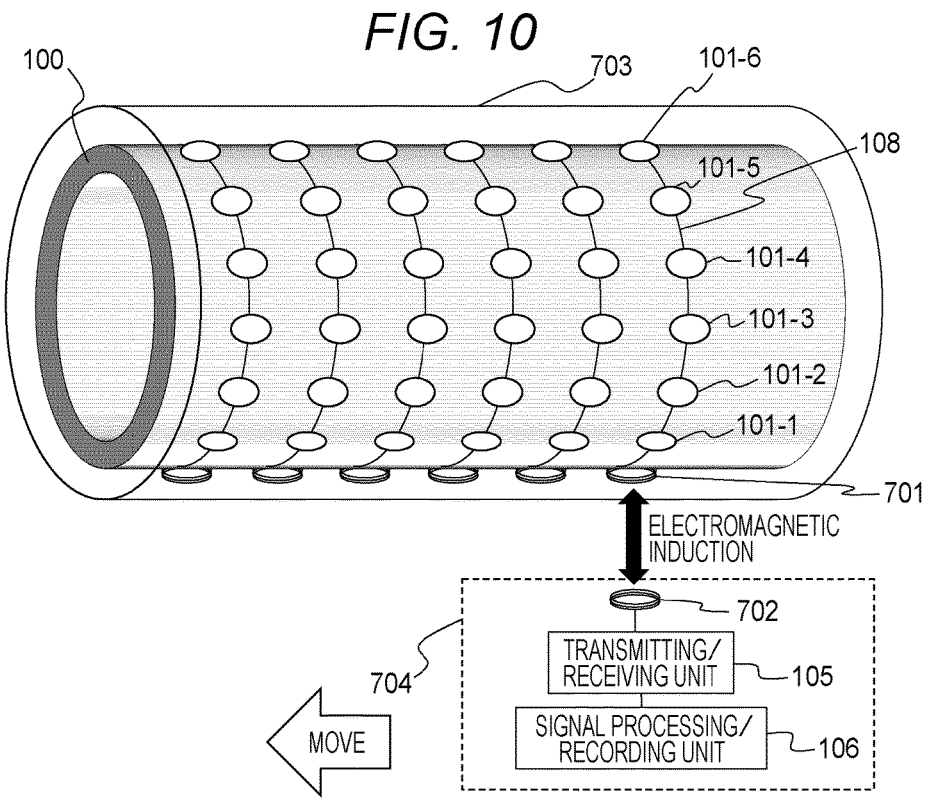
FIG. 10 is a view schematically indicating a state in which an ultrasonic sensor according to a third embodiment of the present invention is attached to a pipe.
Figure 11:
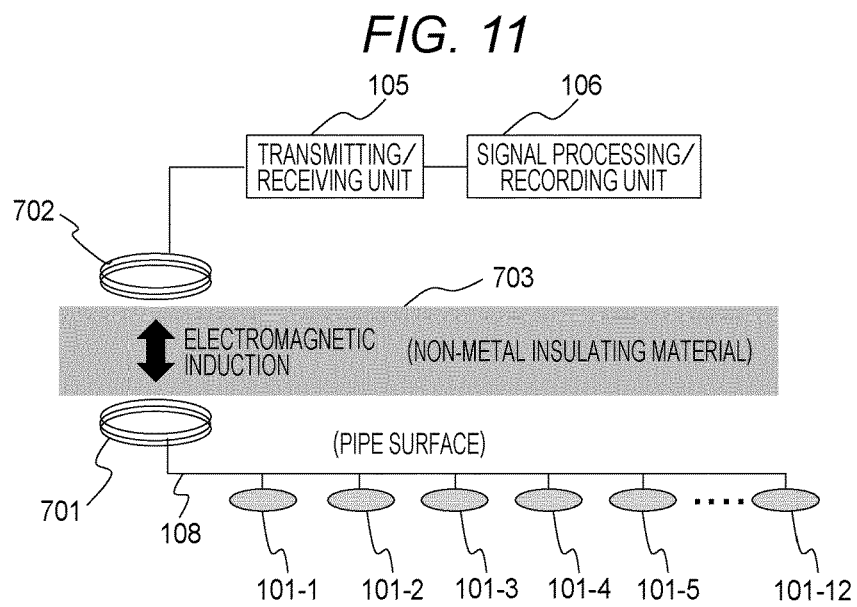
FIG. 11 is a diagram describing the third embodiment.

FIG. 10 is a view schematically indicating a state in which an ultrasonic sensor according to the third embodiment of the present invention is attached to a pipe. FIG. 11 is a view describing the third embodiment. In FIGS. 10 and 11, a non-metal insulating material 703 including a non-metal material is attached around a pipe 100, and between the pipe 100 and the non-metal insulating material 703, a plurality of ultrasonic sensors 101-1 to 101-12 for thickness reduction inspection is attached.

The ultrasonic sensors 101-1 to 101-12 are connected in a circumferential direction, an axial direction, or an arbitrary direction of the pipe 100 by a wiring 108. Further, a part of the wiring 108 is connected to a coil 701 (first coil).

On the other hand, another coil 702 (second coil) is connected to a transmitting/receiving unit 105, and the coils 701 and 702 are disposed opposite to each other by using an electromagnetic induction phenomenon from the outside of the non-metal insulating material 703, and a signal can be transmitted and received between the coils 701 and 702. During measuring, a transmitting/receiving apparatus 704 including the coil 702, the transmitting/receiving unit 105, and the signal processing/recording unit 106 is moved, and an ultrasonic wave signal can be transmitted and received without coming into contact with an insulating material.

The transmitting/receiving apparatus 704 does not necessarily include all of the coil 702, the transmitting/receiving unit 105, and the signal processing/recording unit 106, and a part of them may be included. The other portions are similar to the first embodiment, and therefore a description will be omitted.

In the third embodiment of the present invention, effects as in the first embodiment can be obtained, and also an ultrasonic sensor can transmit and receive a signal without coming into contact with an insulating material of the pipe 100.

Fourth Embodiment

Next, a fourth embodiment of the present invention will be described next.

Figure 12:
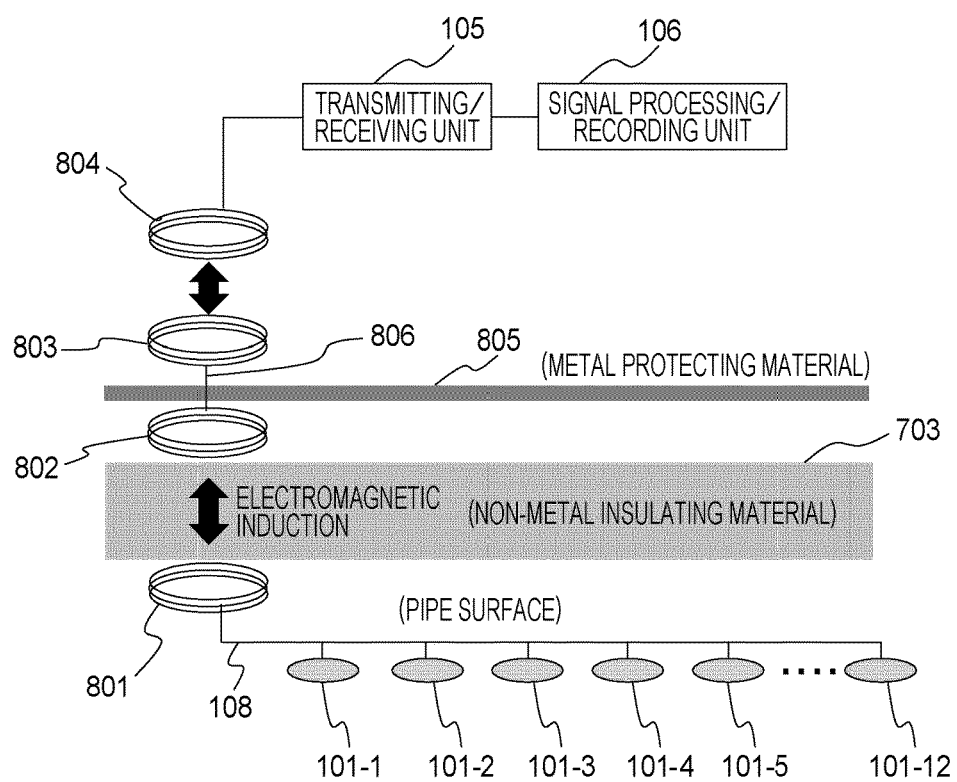
FIG. 12 is a view conceptually indicating a state in which an ultrasonic sensor according to a fourth embodiment of the present invention is attached to a pipe.

FIG. 12 is a view conceptually indicating a state in which an ultrasonic sensor according to the fourth embodiment of the present invention is attached to a pipe. In FIG. 12, a non-metal insulating material 703 including a non-metal material is attached around a pipe 100 (not illustrated in FIG. 12). Further, a metal protection material 805 including a metal material such as aluminum is attached on an outer side of the non-metal insulating material 703 for the purpose of insulation and protection.

The metal protection material 805 may be inserted into the non-metal insulating material 703. As with the configuration illustrated in FIG. 10, a plurality of ultrasonic sensors 101-1 to 101-12 for thickness reduction inspection is attached in a space between a surface of the pipe 100 and the non-metal insulating material 703. The ultrasonic sensors 101-1 to 101-12 are connected by a wiring 108. Further, a part of the wiring 108 is connected to a coil 801 (first coil) disposed on a surface of the pipe 100. Relay coils 802 (second coil) and 803 (third coil) are attached on an inner side and an outer side of the metal protection material 805, and the relay coils 802 and 803 are connected by a wiring 806 penetrating the metal protection material 805.

A coil 804 (fourth coil) is connected to the transmitting/receiving unit 105. The transmitting/receiving unit 105 can transmit and receive a signal with the ultrasonic sensors 101-1 to 101-12 by using an electromagnetic induction phenomenon between coils 801 and 802 disposed opposite to each other and an electromagnetic induction phenomenon between coils 803 and 804 disposed opposite to each other. The other portions are similar to the third embodiment, and therefore a description will be omitted.

In the fourth embodiment of the present invention, effects as in the third embodiment can be obtained, and also a noncontact inspection from the outside of an insulating material including metal disposed on an outer surface of a pipe.

The embodiments described above indicate the case where the present invention is applied to a method and an apparatus for inspecting thickness reduction of a pipe. However, an inspection target of the present invention is not limited to a pipe. For example, the present invention can be applied to a method and apparatus for an ultrasonic thickness reduction inspection method/apparatus for a plate member having a large area.

What is claimed is:

1. An ultrasonic thickness reduction inspection method, comprising:
    disposing a plurality of ultrasonic sensors on a surface of an inspection target;
    exciting the plurality of ultrasonic sensors by a frequency modulated wave signal in which a frequency is changed with time;
    supplying ultrasonic waves to an inside of the inspection target;
    receiving signals in which the plurality of ultrasonic sensors is excited by a plurality of echoes from the inside of the inspection target by the ultrasonic waves supplied to the inside of the inspection target;
    summing the plurality of received echo signals;
    calculating, from cross correlation between the signals summing the plurality of echo signals and the frequency modulated wave signal, a time difference between a first peak of the summed signals and a first peak of the frequency modulated wave signal; and
    detecting a change in a thickness of the inspection target based on the calculated time difference.

2. The ultrasonic thickness reduction inspection method according to claim 1,
    wherein the inspection target is a pipe, and the plurality of ultrasonic sensors is disposed side by side in a circumferential direction of the pipe.

3. The ultrasonic thickness reduction inspection method according to claim 1,
    wherein the inspection target is a pipe, and the plurality of ultrasonic sensors is disposed side by side in an axial direction of the pipe.

4. The ultrasonic thickness reduction inspection method according to claim 1, wherein the inspection target is a pipe, and the plurality of ultrasonic sensors is disposed side by side in a circumferential direction and an axial direction of the pipe.

5. The ultrasonic thickness reduction inspection method according to claim 1,
wherein, by electromagnetic induction generated between a plurality of coils disposed opposite to each other, signals are received which are generated when the frequency modulated wave signals of the plurality of ultrasonic sensors are excited, and the plurality of ultrasonic sensors is excited by the plurality of echoes from the inside of the inspection target.

6. The ultrasonic thickness reduction inspection method according to claim 1,
wherein a first coil connected to the plurality of ultrasonic sensors, a second coil disposed opposite to the first coil, a third coil electrically connected to the second coil via a metal protection material, and a fourth coil disposed opposite to the third coil are disposed, and by electromagnetic induction between the first coil and the second coil and electromagnetic induction between the third coil and the fourth coil, signals are received which are generated when the plurality of ultrasonic sensors is excited by frequency modulated wave signals, and the plurality of ultrasonic sensors is excited by the plurality of echoes from the inside of the inspection target.

7. An ultrasonic thickness reduction inspection apparatus, comprising:
a plurality of ultrasonic sensors disposed on a surface of an inspection target;
a transmitter/receiver configured to excite the plurality of ultrasonic sensors by a frequency modulated wave signal in which a frequency is changed with time, to supply ultrasonic waves to an inside of the inspection target, and to receive signals in which the plurality of ultrasonic sensors is excited by a plurality of echoes from the inside of the inspection target by the ultrasonic waves supplied to the inside of the inspection target; and
a signal processor/recorder configured to sum the plurality of echo signals received by the transmitter/receiver, to calculate a time difference between a first peak of the summed signal and a first peak of the frequency modulated wave signal from cross correlation between signals summing the plurality of echo signals and the frequency modulated wave signal, and to detect a change in a thickness of the inspection target based on the calculated time difference.

8. The ultrasonic thickness reduction inspection apparatus according to claim 7,
wherein the inspection target is a pipe, and the plurality of ultrasonic sensors is disposed side by side in a circumferential direction of the pipe.

9. The ultrasonic thickness reduction inspection apparatus according to claim 7,
wherein the inspection target is a pipe, and the plurality of ultrasonic sensors is disposed side by side in an axial direction of the pipe.

10. The ultrasonic thickness reduction inspection apparatus according to claim 7,
wherein the inspection target is a pipe, and the plurality of ultrasonic sensors is disposed side by side in a circumferential direction and an axial direction of the pipe.

11. The ultrasonic thickness reduction inspection apparatus according to claim 7, further comprising:
a first coil connected to the plurality of ultrasonic sensors; and
a second coil disposed opposite to the first coil and connected to the transmitter/receiver,
wherein, by electromagnetic induction generated between the first coil and the second coil, signals are received which is generated when the plurality of ultrasonic sensors is excited by a frequency modulated wave signal, and the plurality of ultrasonic sensors is excited by the plurality of echoes from the inside of the inspection target.

12. The ultrasonic thickness reduction inspection apparatus according to claim 7, further comprising:
a first coil connected to the plurality of ultrasonic sensors;
a second coil disposed opposite to the first coil;
a third coil electrically connected to the second coil via a metal protection material; and
a fourth coil disposed opposite to the third coil and connected to the transmitter/receiver,
wherein, by electromagnetic induction generated between the first coil and the second coil and electromagnetic induction between the third coil and the fourth coil, signals are received which are generated when the plurality of ultrasonic sensors is excited by a frequency modulated wave signal, and the plurality of ultrasonic sensors is excited by the plurality of echoes from the inside of the inspection target.

* * * * *